United States Patent
Chen et al.

(10) Patent No.: US 9,549,797 B2
(45) Date of Patent: Jan. 24, 2017

(54) DENTAL PASTE DISPENSING DEVICE AND METHOD OF USE

(75) Inventors: Xiangxu Chen, Diamond Bar, CA (US); James Lobsenz, Redondo Beach, CA (US); Beat Kilcher, Bosco Luganese (CH)

(73) Assignee: Kerr Corporation, Orange, CA (US)

( * ) Notice: Subject to any disclaimer, the term of this patent is extended or adjusted under 35 U.S.C. 154(b) by 945 days.

(21) Appl. No.: 13/214,933

(22) Filed: Aug. 22, 2011

(65) Prior Publication Data

US 2012/0045732 A1 Feb. 23, 2012

Related U.S. Application Data

(60) Provisional application No. 61/375,605, filed on Aug. 20, 2010.

(51) Int. Cl.
*A61C 19/06* (2006.01)
*A61C 5/06* (2006.01)

(52) U.S. Cl.
CPC ............. *A61C 19/063* (2013.01); *A61C 5/062* (2013.01)

(58) Field of Classification Search
CPC .............................. A61C 19/063; A61C 5/062
USPC ..................................................... 433/90, 215
See application file for complete search history.

(56) References Cited

U.S. PATENT DOCUMENTS

| | | | | |
|---|---|---|---|---|
| 1,951,544 A * | 3/1934 | Burrell | ......................... | 222/490 |
| 2,753,091 A * | 7/1956 | Herzig | ......................... | 222/491 |
| 2,904,225 A * | 9/1959 | Earles, Jr. | ..................... | 222/183 |
| 3,342,318 A * | 9/1967 | Ruekberg et al. | ............ | 206/540 |
| 3,610,477 A * | 10/1971 | Herzig | ......................... | 222/494 |
| 3,825,157 A * | 7/1974 | Herzig | ......................... | 222/494 |
| 4,553,686 A * | 11/1985 | Dougherty | .................... | 222/212 |
| 4,619,613 A * | 10/1986 | Dragan | ........................... | 433/90 |
| 4,917,267 A * | 4/1990 | Laverdure | ..................... | 222/107 |
| 5,398,853 A * | 3/1995 | Latham | ......................... | 222/491 |
| 5,529,224 A * | 6/1996 | Chan et al. | .................... | 222/212 |
| 6,170,714 B1 | 1/2001 | Lesage | | |
| 6,682,348 B2 * | 1/2004 | Lawter | .................. | A61C 5/062 433/90 |
| 6,929,157 B2 | 8/2005 | Orecchia et al. | | |
| 6,945,436 B2 | 9/2005 | Mayer | | |
| 2003/0013066 A1* | 1/2003 | Dragan et al. | .................. | 433/90 |
| 2005/0202367 A1* | 9/2005 | Kollefrath et al. | ........... | 433/136 |
| 2011/0151403 A1 | 6/2011 | Pauser et al. | | |
| 2011/0217670 A1* | 9/2011 | Walter et al. | ................... | 433/82 |

* cited by examiner

*Primary Examiner* — Cris L Rodriguez
*Assistant Examiner* — Hao D Mai
(74) *Attorney, Agent, or Firm* — Wood Herron & Evans LLP

(57) ABSTRACT

A dental paste dispensing device having a modified dispensing end for atraumatic contact with soft tissue is disclosed. The dispensing device has a needle with an attachment end adapted to be attached to a capsule containing the dental paste and a dispensing end with a terminal edge for dispensing the dental paste to a location in a patient mouth containing soft tissue, wherein the dispensing end includes an atraumatic modification. The modification is a plastic tip member over the dispensing end having a flattened static position and a rounded dynamic position.

5 Claims, 3 Drawing Sheets

400# DENTAL PASTE DISPENSING DEVICE AND METHOD OF USE

CROSS-REFERENCE TO RELATED APPLICATION

Pursuant to 37 C.F.R. §1.78(a)(4), this application claims the benefit of and priority to prior filed co-pending Provisional Application Ser. No. 61/375,605, filed Aug. 20, 2010, which is expressly incorporated herein by reference.

FIELD OF THE INVENTION

This invention relates to a dispensing device for use in delivering a paste in a dental procedure.

BACKGROUND OF THE INVENTION

The restoration of a patient's tooth or teeth often includes the replacement of natural tooth structure by a manufactured dental restoration or dental prosthesis. Typically, a tooth that is to be restored is first prepared by a dentist to remove undesired tooth substance and to provide the tooth with a shape appropriate to receive the dental restoration. The dental restoration is typically mated precisely with the remaining tooth shape prepared by the dentist on the basis of an impression of the prepared tooth. Therefore the dental impression should be very precise, and should represent all tooth structure required to determine the shape of the mating surface of the later dental restoration. In particular, the dental impression should represent the transition or the "margin" between the shape prepared in a tooth and the natural tooth shape. For dental restorations that extend below a patient's gingiva (or gums), the dentist also should make the part of the margin accessible for the dental impression that would normally be covered by the gingiva. The procedure of displacing the gingiva from the tooth to make the margin accessible is also known as "gingival retraction" in the field of dentistry.

A common gingival retraction procedure includes the insertion of a retraction cord in the gingival sulcus, which displaces the gingiva from the tooth. However, the insertion of a retraction cord is relatively time consuming and is generally perceived as being relatively inconvenient for the dentist and uncomfortable for the patient. An alternative for the retraction cord is a gingival retraction paste, which is typically a high viscosity paste that is squeezed or injected into the gingival sulcus, thereby displacing the soft gingival tissue from the tooth. The gingival retraction paste in one example is provided in a syringe or applicator that is connectable with a metal dispensing cannula or needle. The cannula or needle dispenses the paste around a tooth towards the entry of the gingival sulcus to thereby squeeze it into the gingival sulcus.

However, soft tissue in the mouth is very sensitive and trauma to the tissue can occur when a metal device makes contact. This issue may also occur in other dental procedures besides gingival retraction, where dental paste is being applied in a region containing soft tissue that may be contacted by the dispensing end of the device. There is thus a need for an improved dispensing device for providing dental paste to a region with soft tissue.

SUMMARY OF THE INVENTION

The present invention provides a dental paste dispensing device having a modified dispensing end for atraumatic contact with soft tissue. To that end, the dispensing device comprises a metal needle having an attachment end adapted to be attached to a capsule containing the dental paste and a dispensing end with a terminal edge for dispensing the dental paste to a location in a patient mouth containing soft tissue, wherein the dispensing end includes a modification for atraumatic contact with the soft tissue. The modification comprises one of a non-metal coating on an outer surface of the dispensing end, a plastic tip member over the dispensing end, or a decreasing diameter at the terminal edge from a first point on the outer surface to a distal-most point of the outer surface. In one embodiment, the metal needle has a dispensing end coated with a rubbery material. In another embodiment, the metal needle has a rounded or slanted terminal edge at the dispensing end. In yet another embodiment, the metal needle includes a plastic tip attached thereto having an inner channel with a flattened oval shape in a static position and a rounded shape in a dynamic position with sidewall bumps adjacent the inner channel for displacing soft tissue.

A method for delivering a dental paste to an oral location comprising soft tissue is also provided. The method comprises loading a capsule of dental paste into a carrier of an applicator having a plunger adapted to enter a first end of the carrier for engaging the capsule, and positioning a metal needle attached to the capsule such that an attachment end of the needle is proximate a second end of the carrier opposite the first end and a dispensing end of the needle having a terminal edge is distal to the carrier. The dispensing end of the metal needle includes the modification for atraumatic contact with the soft tissue, as discussed in the embodiments of the dispensing device. The method further comprises contacting the soft tissue with the dispensing end while advancing the plunger to dispense the dental paste from the dispensing end of the needle into the oral location while the modification prevents traumatic injury to the soft tissue.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

In accordance with embodiments of the invention, the shape, material, and/or dimensions of the needle tip of a dispensing device may help to avoid damage to soft tissue during use of the device of the invention in a patient's mouth. One use is a gingival retraction procedure in which the device dispenses dental paste into the gingival sulcus between a tooth and the gums (gingiva). The invention also may allow the dental paste to be inserted relatively deep into the gingival sulcus, without causing trauma to the soft tissue. Deep penetration of the dental paste in the gingival sulcus may help to effectively retract the gingiva from a tooth, and consequently may help to provide an acceptable impression particularly of a preparation margin of a tooth. Other dental procedures may likewise involve application of a dental paste to oral locations with soft tissue, whereby a modification to the needle tip in accordance with the invention prevents trauma to the soft tissue.

Figure 1:
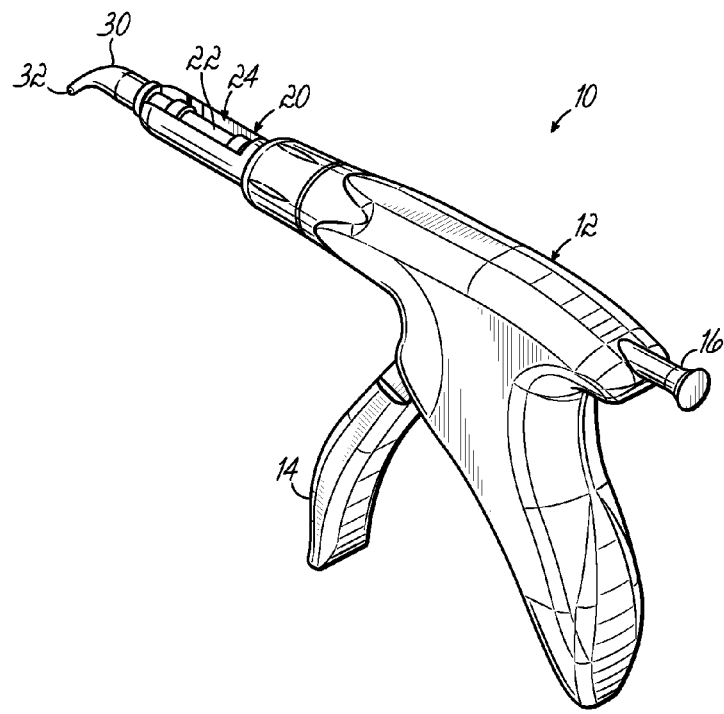
FIG. 1 is a perspective view of a dispensing applicator having a detachable carrier and body.

FIG. 1 is a perspective view of a dispensing applicator 10 for use in dispensing a flowable material (i.e., dental paste) in a dental procedure. The applicator 10 includes a body 12 with gears, which body may be anatomically designed for easy gripping by the hand and convenient squeezing of trigger 14 to actuate a piston 16 for dispensing dental paste, with a force advantage, for example, of at least 9 to 1. The applicator 10 further includes a detachable carrier 20 for receiving a capsule 22 containing the dental paste, such as a gingival retraction material. In one embodiment, the carrier 20 is detached from the body 12 by screwing. The piston 16 extends through body 12 and is received in a chamber 24 of carrier 20 to engage a capsule 22 residing therein for advancing the dental paste. The capsule 22 includes a cannula or needle 30 terminating distally in an end that serves as a dispensing end 32 for applicator 10 from which the dental paste may be dispensed.

FIGS. 2-8 describe a carrier 20 for attachment to body 12 and which includes chamber 24 for receiving a capsule 22. The carrier 20 may include a slot or groove 26 for receiving a mating member 28 of capsule 22, and which prevents the capsule 22 from falling off. In one embodiment, the carrier 20 may be used for two different lengths of filled capsules 22. In one embodiment, the carrier is detachable from the body of the applicator.

In one embodiment, the capsule 22 is filled with paste for dental use. The device 10 may use a capsule 22 having an integrated needle 30 made of the same plastic material as the capsule 22, as depicted in FIG. 1, and which may or may not be removable. The needle 30 made of plastic provides an atraumatic contact with soft tissue, as opposed to a metal needle. The plastic needle 30 can thus be used in a gingival retraction procedure for displacing the gingiva laterally without trauma to the gingiva, and thereby allowing for delivery of the retraction paste deep into the gingival sulcus. Alternatively, the needle 30 may be removable and of a different material than the capsule 22, such as a metal needle. The needle 30 may extend at an angle from the capsule 22, either straight or curved, or may be co-aligned and/or parallel with an axis of the capsule 22. The configuration may be selected for suitability in reaching certain locations in a patient's mouth.

Figure 9:
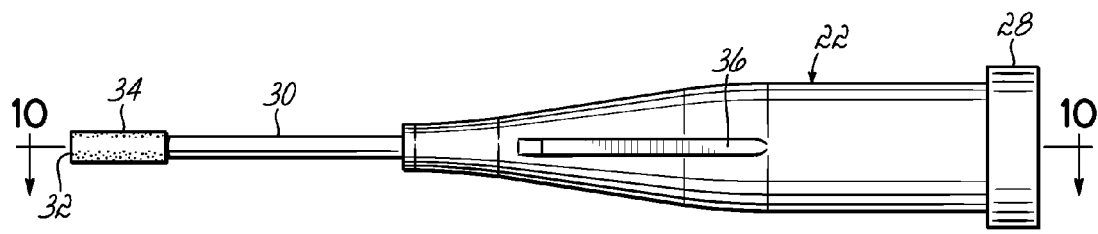
FIG. 9 is a side view of a capsule and needle according to one embodiment.
Figure 10:
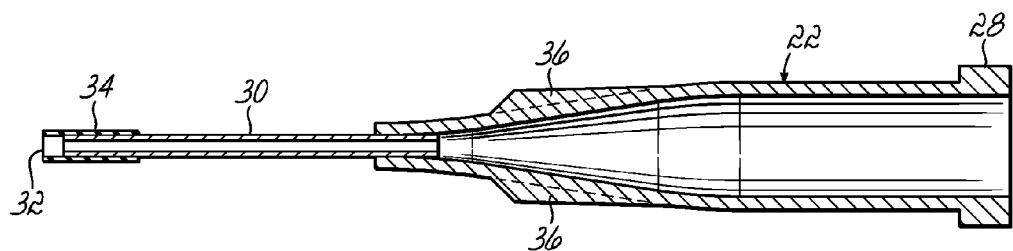
FIG. 10 is a cross-sectional view taken along line 10-10 of FIG. 9.
Figure 2:
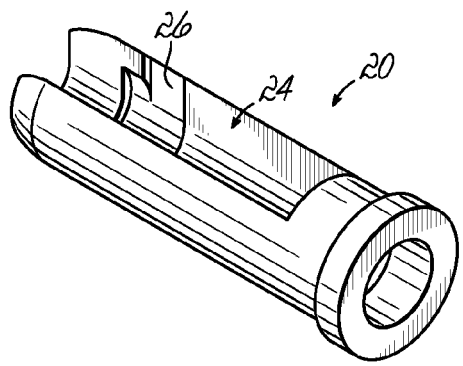
FIG. 2 is a perspective view of a detachable carrier.
Figure 3:
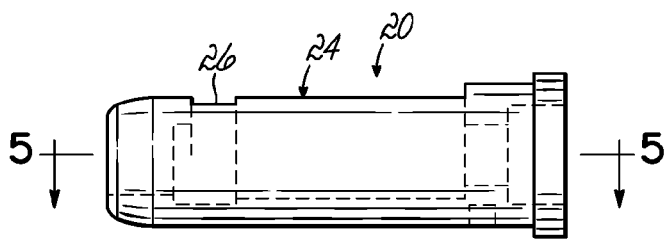
FIG. 3 is a side view of the carrier of FIG. 2.
Figure 4:
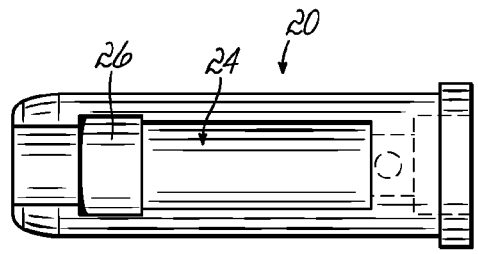
FIG. 4 is a top view of the carrier of FIG. 2.
Figure 7:
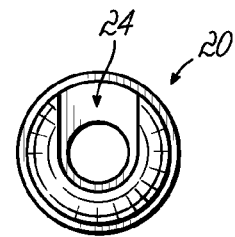
FIG. 7 is a front view of the carrier of FIG. 2.
Figure 5:
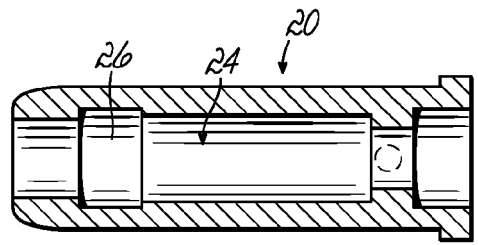
FIG. 5 is a cross-sectional view taken along line 5-5 of FIG. 3.
Figure 8:
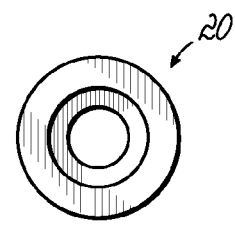
FIG. 8 is a rear view of the carrier of FIG. 2.
Figure 6:
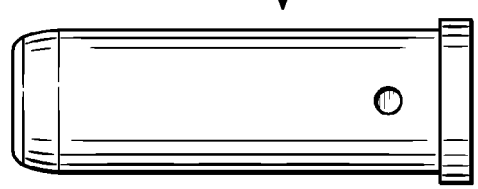
FIG. 6 is a bottom view of the carrier of FIG. 2.

FIG. 9 depicts an atraumatic design for a needle 30 adapted to be attached to a capsule 22 according to an embodiment of the invention for delivering paste material for dental use. FIG. 10 is a cross-sectional view taken along line 10-10 of FIG. 9. In one embodiment, the capsule 22 has a metal needle 30 that is permanently attached. In one embodiment, the capsule 22 has a metal needle 30 that is temporarily (removably) attached by means of screw-on, click-on or click-and-twist-on immediately before use. The dispensing end 32 of the metal needle 30 includes a non-metal coating 34, for example of a rubbery material. The rubbery material can prevent tissue trauma when it is in contact with soft tissue in a dental procedure. In one embodiment, the capsule 22 has a number of wings 36 for ease of twist. In one embodiment, the capsule 22 is used with a dispensing applicator, such as applicator 10 of FIG. 1.

The non-metal coating 34 may be spray-coated, dip-coated, or over-molded onto the dispensing end 32, and advantageously covers the terminal edge of the metal needle 30, so that upon contact with the soft tissue, no metal touches the soft tissue. Any other suitable means of applying a non-metal coating 34 to a metal needle 30 may be employed other than the means recited above, whether now known or hereafter developed. The non-metal coating 34 may be a rubbery material, such as natural or synthetic rubber, polyethylene, polyethylene propylene, or any other elastomer suitable for use in an oral environment.

Figure 11:
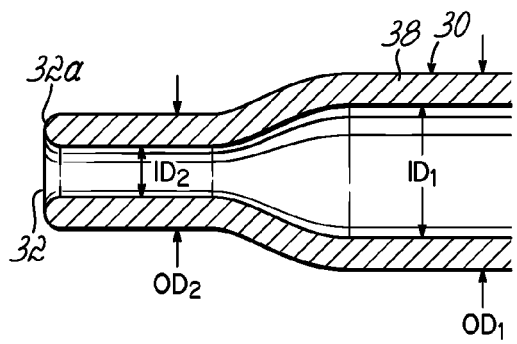
FIG. 11 is a cross-sectional view of a needle according to another embodiment.

FIG. 11 is a cross-sectional view of an alternative atraumatic configuration for the dispensing end 32 of a metal needle 30. The needle wall 38 may taper inwardly in diameter approaching the dispensing end 32 and terminates in a rounded edge 32a. Thus, an inner diameter $ID_1$ adjacent a proximal attachment end (not shown) of the needle 30 that attaches to the capsule 22 may be greater than an inner diameter $ID_2$ at the opposing distal dispensing end 32. Likewise, an outer diameter $OD_1$ adjacent the attachment end of the needle 30 may be greater than an outer diameter $OD_2$ at the dispensing end 32. At the terminal edge 32a of the needle 30, i.e., the distal-most portion of the needle 30, the outer surface tapers inwardly in curved fashion, i.e., the outer diameter $OD_2$ decreases non-linearly to a smaller diameter at the terminal edge 32a. In one embodiment, the outer diameter $OD_2$ decreases gradually until reaching the inner diameter $ID_2$ such that only the outer surface of the needle 30 is radiused at the terminal edge 32a. In another embodiment, the inner surface also tapers outwardly in curved fashion, i.e., the inner diameter $ID_2$ increases non-linearly as the outer diameter $OD_2$ decreases non-linearly until an intermediate diameter is reached, such that the terminal edge 32a is radiused both on the inner and outer surfaces of the needle 30. The smaller diameters $ID_2/OD_2$ and rounded terminal edge 32a provide a non-traumatic dispensing end 32a when in contact with soft tissue in the mouth, and can thus permit the needle 30 to contact the gingiva and displace it laterally to inject the dental paste into the gingival sulcus. Because the terminal edge 32a is rounded, i.e., it has a radius with no sharp corners, it gently slides against the soft tissue, and in particular can slide between a tooth and the gum, without harshly engaging the soft tissue, thereby allowing for the dental paste to be dispensed deeply into the gingival sulcus. It may be appreciated, that the rounded edge 32a alone provides an atraumatic dispensing end 32 for needle 30, such that a constant diameter needle wall 38 is also contemplated, with the diameter of the needle varying only at the terminal edge 32a.

Figure 12:
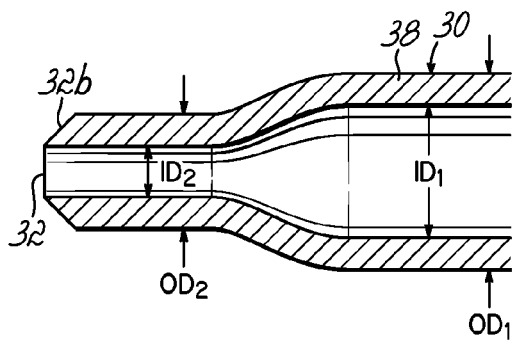
FIG. 12 is a cross-sectional view of a needle according to another embodiment.
Figure 13:
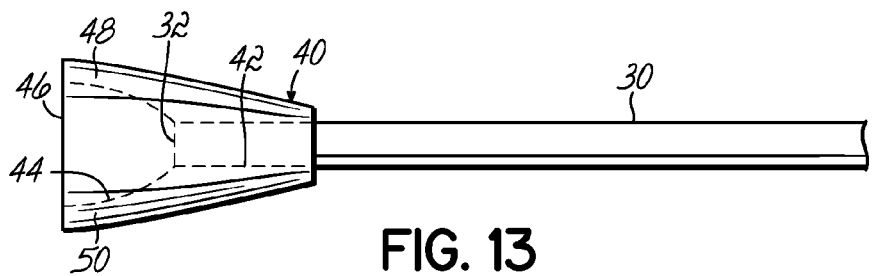
FIG. 13 is a top view of a needle with plastic tip according to another embodiment.
Figure 14:
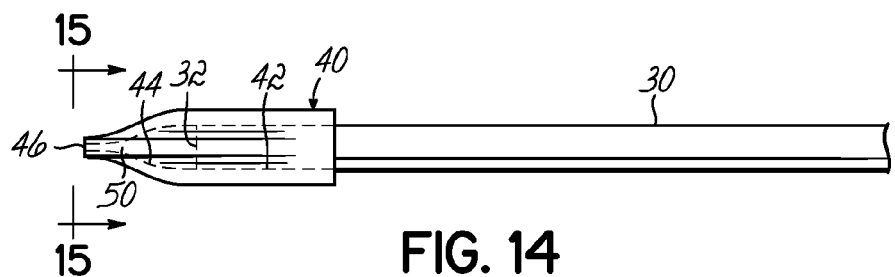
FIG. 14 is a side view of the needle with plastic tip of FIG. 13.
Figure 15:
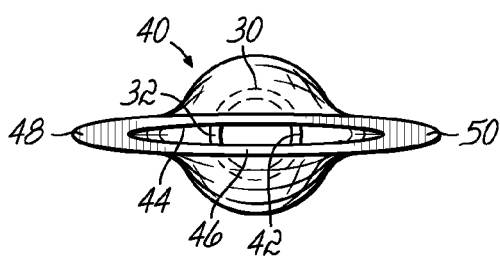
FIG. 15 is an end view of the needle with plastic tip, in the static position, taken along line 15-15 of FIG. 14.
Figure 16:
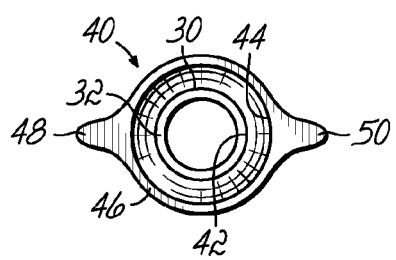
FIG. 16 is an end view of the needle with plastic tip, in the dynamic position.

FIG. 12 is a cross-sectional view of yet another alternative atraumatic configuration for the dispensing end 32 of a metal needle 30. As with the needle 30 of FIG. 11, the needle wall 38 may taper inwardly in diameter approaching the dispensing end 32, such that the inner diameter $ID_1$ and an outer diameter $OD_1$ may be greater than the inner diameter $ID_2$ and outer diameter $OD_2$, respectively. The needle 30, however, terminates in a straight angled, inwardly slanted edge 32b formed by the $OD_2$ linearly decreasing until becoming essentially equal to the $ID_2$ at the dispensing end 32. In other words, the terminal edge 32b of the needle 30 slants inwardly from the outer diameter $OD_2$ to the inner diameter $ID_2$, thereby forming an inwardly slanted terminal edge 32b for the needle 30. The inwardly slanted terminal edge 32b of the dispensing end 32 provides a non-traumatic dispensing end 32 when in contact with soft tissue in the mouth, and can thus permit the needle 30 to contact the gingiva and displace it laterally to inject the dental paste into the gingival sulcus. Because the terminal edge 32b is slanted, upon contacting the soft tissue with the edge 32b, the soft tissue gently slides along the slanted edge 32b rather than being harshly engaged by it, allowing the dispensing end 32 to slip gently between the tooth and gums for dispensing the dental paste deeply into the gingival sulcus. Again, a needle wall 38 of constant diameter from the attachment end to the slanted terminal edge 32b of the dispensing end 32 is contemplated, with the slanted terminal edge 32b providing an atraumatic dispensing end 32.

Both FIGS. 11 and 12 generally disclose a modification to a metal needle 30 in which the outer surface decreases in diameter at the dispensing end 32, from a first point to a second distal-most point. The decrease in diameter can be non-linear to provide the radiused terminal edge 32a, or linear to provide the slanted terminal edge 32b, either modification providing an atraumatic dispensing end 32 for contacting soft tissue in a dental procedure. In addition, or alternatively, the dispensing end 32, including the terminal edge 32a, 32b, can be coated with a non-metal coating 34, as shown in FIGS. 9 and 10, in particular a rubbery material, to provide an atraumatic modification to the dispensing end 32 of a metal needle 30.

FIGS. 13-16 detail yet another alternative atraumatic configuration for the dispensing end 32 of a metal needle 30. A plastic tip 40 is placed over the dispensing end 32 of needle 30. The plastic tip 40 includes a first inner channel 42 sized to fit securely over the dispensing end 32 of needle 30 and is attached thereto. A second inner channel 44 then forms the dispensing end 46 of the plastic tip 40, and is advantageously slightly larger than the inner diameter $ID_2$ of the needle 30 to avoid rupturing the plastic tip when a dental paste is extruded through the dispensing ends 32 and 46. Sidewall bumps 48, 50 are provided on either side of the second inner channel 44. In the static (i.e., non-dispensing) position, shown in end view in FIG. 15, the second inner channel 44 forms a flattened oval shape. In the dynamic (i.e., dispensing) position, shown in end view in FIG. 16, the second inner channel 44 adapts to a round shape with the sidewall bumps 48, 50 protruding therefrom. The sidewall bumps 48, 50 assist with pushing the gingiva away from the tooth laterally in a non-traumatic fashion, so that the dental paste is guided into the gingival sulcus.

FIGS. 9-16 are described with reference to a metal needle 30; however, the invention is not so limited. The modifications to the dispensing end 32 of a needle 30 may also be employed with a plastic needle to further ensure atraumatic delivery of a dental paste. However, these modifications may not be considered necessary, as a plastic material may by itself be sufficiently atraumatic when contacting soft tissue, such as the gingiva during gingival retraction.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A method for delivering a dental paste to an oral location comprising soft tissue, comprising:
    loading a capsule of dental paste into a carrier of an applicator having a plunger adapted to enter a first end of the carrier for engaging the capsule;
    positioning a metal needle attached to the capsule such that an attachment end of the needle is proximate a second end of the carrier opposite the first end and a dispensing end of the needle having a terminal edge is distal to the carrier, wherein the dispensing end includes a modification for atraumatic contact with the soft tissue, where the modification comprises a plastic tip member over the dispensing end, comprising a first inner channel engaged over the dispensing end and a second inner channel of larger size than an inner diameter of the dispensing end, where the second inner channel has a flattened oval shape in a static position and a rounded shape in a dynamic position;
    contacting the soft tissue with the dispensing end while advancing the plunger to dispense the dental paste from the dispensing end of the needle into the oral location while the modification prevents traumatic injury to the soft tissue.

2. The method of claim 1, wherein the plastic tip member further includes a pair of opposed sidewall bumps adjacent and protruding outwardly from the second inner channel for displacing gingiva during delivery of the dental paste.

3. The method of claim 1, wherein the soft tissue is gingival tissue and the oral location is a gingival sulcus, and wherein the contacting and dispensing laterally displaces the gingival tissue.

4. A method for delivering a dental paste to a gingival sulcus, comprising:
    loading a capsule of dental paste into a carrier of an applicator having a plunger adapted to enter a first end of the carrier for engaging the capsule;
    positioning a needle attached to the capsule such that an attachment end of the needle is proximate a second end of the carrier opposite the first end and a dispensing end of the needle having a terminal edge is distal to the carrier, wherein the dispensing end includes a modification for atraumatic contact with gingiva, where the modification comprises a plastic tip member over the dispensing end, the plastic tip member comprising a first inner channel engaged over the dispensing end and a second inner channel of larger size than an inner diameter of the dispensing end, where the second inner channel has a flattened oval shape in a static position and a rounded shape in a dynamic position;
    contacting the gingiva adjacent the gingival sulcus with the dispensing end to laterally displace the gingiva atraumatically while advancing the plunger to dispense the dental paste from the dispensing end of the needle into the gingival sulcus.

5. The method of claim 4, wherein the plastic tip member further includes a pair of opposed sidewall bumps adjacent and protruding outwardly from the second inner channel for displacing gingiva during delivery of the dental paste.

* * * * *